(12) United States Patent
Embleton

(10) Patent No.: US 6,297,240 B1
(45) Date of Patent: Oct. 2, 2001

(54) METHOD FOR TREATING OPHTHALMIC DISEASE THROUGH FAST DISPERSING DOSAGE FORMS

(75) Inventor: Jonathan Kenneth Embleton, Cirencester (GB)

(73) Assignee: R.P. Scherer Limited (GB)

( * ) Notice: Subject to any disclaimer, the term of this patent is extended or adjusted under 35 U.S.C. 154(b) by 0 days.

(21) Appl. No.: 09/246,381

(22) Filed: Feb. 8, 1999

Related U.S. Application Data

(63) Continuation of application No. PCT/GB97/02086, filed on Aug. 4, 1997.

(30) Foreign Application Priority Data

Aug. 8, 1996 (GB) .................................................. 9616672

(51) Int. Cl.$^7$ ................................................. A61K 31/535
(52) U.S. Cl. ........................ 514/236.2; 514/912; 514/913
(58) Field of Search .............................. 514/236.2, 912, 514/913

(56) References Cited

U.S. PATENT DOCUMENTS 4,600,708 * 7/1986 Reuter et al. .

FOREIGN PATENT DOCUMENTS 0 107 941 * 9/1984 (EP) .
0 215 635 A2 * 3/1987 (EP) .
0 627 218 A1 * 8/1993 (EP) .
0 614 659 A2 * 9/1994 (EP) .
WO 87/04342 * 7/1987 (WO) .

OTHER PUBLICATIONS

Database XP 002028901 and JP 59 059 610 A, Apr. 5, 1984, Japan.*
Database XP 002028902 and JP 01 203 336 A, Aug. 16, 1989, Japan.*
Patent Abstracts of Japan vol. 10, No. 269 and JP 61 093113 A, May 12, 1986, Japan.*
Patent Abstracts of Japan vol. 13, No. 156 and JP 63 310817 A, Dec. 19, 1988, Japan.*
B. Taylan et al., "Design and evaluation of sustained–release and buccal adhesive propranolol hydrochloride tablets", Journal of Controlled Release, vol. 38, No. 1, Jan. 1996, Amsterdam (NL), pp. 11–20 XP000543705.*

* cited by examiner

*Primary Examiner*—Zohreh Fay
(74) *Attorney, Agent, or Firm*—Donald O. Nickey; Daniel N. Christus

(57) ABSTRACT

This invention relates to pharmaceutical compositions for oral administration comprising a carrier and, as active ingredient, an ophthalmologically active compound, characterized in that the composition is formulated to promote pre-gastric absorption of the ophthalmologically active compound. A process for preparing such compositions and the use of such compositions for the treatment of ophthalmic diseases, particularly diseases caused by elevated introocular pressure, such as ocular hypertension and glaucoma, are also provided.

10 Claims, No Drawings

METHOD FOR TREATING OPHTHALMIC DISEASE THROUGH FAST DISPERSING DOSAGE FORMS

This Application is a continuation of International Application No. PCT/GB97/02086, filed Aug. 4, 1997, now pending (which is hereby incorporated by reference).

DESCRIPTION

TECHNICAL FIELD

This invention relates to pharmaceutical compositions, a process for preparing such compositions and the use of such compositions for the treatment of ophthalmic diseases, particularly diseases caused by elevated intra-ocular pressure, such as ocular hypertension and glaucoma.

BACKGROUND OF THE INVENTION

Ophthalmic medicines are most frequently formulated as ophthalmic treatment fluids which are commonly administered to the eye by means of eye drops or ointment. The use of eye drops has a number of disadvantages, primarily as a consequence of the difficulty with which drops are accepted by the patient. The drops are relatively large, and the instinctive blink that is provoked by the arrival of a drop on the eye severely limits the amount of or proportion of fluid that actually contacts the target area on the eye. Typically less than 10% of a 50 µl drop is effective, the remainder being lost by drainage, either externally or through nasolacrimal drainage. Such use of expensive treatment fluids is wasteful, as well as leading to substantial uncertainty regarding the effectiveness of a treatment since the delivery of a drop of a particular size requires considerable manual dexterity. Similar problems apply in the use of ointments, although levels of wastage can be reduced by careful delivery and, the greater viscosity of ointments reduces their tendency to drain or be washed away.

Another problem is that ophthalmic dropper bottles are difficult to use with any degree of accuracy since the delivery of a drop of a particular size requires considerable manual dexterity. Also, it is difficult, if not impossible, for the patient to see where the eye drops are to be instilled. Consequently, underdosing or overdosing frequently occurs. Indeed, since the majority of patients suffering from glaucoma are over 70 years of age and may have other health problems such as stroke, poor vision, arthritis, poor physical coordination etc., the use of an ophthalmic dropper bottle is often not a viable option for such patients. This problem is further exacerbated by the fact that many such patients live alone and may have difficulty in obtaining help in the administration of their medication.

Additionally, eye drops typically incorporate preservatives to prevent growth of microorganisms. These preservatives can cause irritation to the eyes of some patients. The unit dose oral system obviates the requirement for these potentially irritant preservatives.

A further disadvantage of eye drops is that their extended use can have a deleterious effect on the outcome of later corrective surgery.

Some attempts have been made to administer certain ophthalmic medicines, such as certain beta-adrenoceptor blocking agents, orally in the form of conventional tablets. However, the ophthalmic therapeutic effect of such medicines tends to be significantly reduced by slow and/or incomplete absorption followed by presystemic metabolism of the active ingredient in the tissues of the small intestine and/or liver (the first pass effect). Also, such conventional oral administration tends to produce other effects associated with beta-adrenoceptor blocking agents, such as markedly reduced systemic blood pressure and pulse rate, which are undesirable in the treatment of glaucoma as optic nerve perfusion may be reduced.

A recent clinical study by Sadig and Vernon (British Journal of Ophthalmology, 1996, 80, 532–535) showed that an ophthalmic solution of timolol maleate produced a substantial reduction in intra-ocular pressure following sub-lingual administration. This reduction in intra-ocular pressure was seen in both eyes simultaneously and was comparable to the reduction in intra-ocular pressure achieved by topical application of the same formulation whereas topical administration produced a marked reduction in intra-ocular pressure only in the treated eye. The lowering of intra-ocular pressure in both eyes is usually desirable as diseases characterized by elevated intra-ocular pressure normally occur simultaneously in both eyes. However, small drops of aqueous formulation are not a convenient way by which to administer drugs sub-lingually, particularly for patients suffering from glaucoma, as it is difficult for the patient to see the area to which the drops must be delivered and, as discussed above, dropper bottles are difficult to use and do not deliver an accurate dose of is the active ingredient.

It is therefore apparent from the above that it would be highly desirable from a clinical perspective to find a way of administering ophthalmic medicines which is easy for the patient to accomplish, which ensures the delivery of an accurate unit dose and which provides for rapid systemic absorption without significant first pass metabolism so that the bioavailability of the active ingredient is enhanced.

SUMMARY OF THE INVENTION

According to the present invention there is therefore provided a pharmaceutical composition for oral administration comprising a carrier and, as active ingredient, an ophthalmologically active compound, characterized in that the composition is formulated to promote pre-gastric absorption of the ophthalmologically active compound.

The term "pre-gastric absorption" is used to refer to absorption of the active ingredient from that part of the alimentary canal prior to the stomach and includes buccal, sublingual, oropharyngeal and esophageal absorption.

It is envisaged that such pre-gastric absorption will occur primarily across the mucous membranes in the mouth, pharynx and oesophagus. Accordingly, it is preferred that the composition of the invention is formulated to promote absorption of the ophthalmologically active compound through the buccal, sublingual, pharyngeal and/or esophageal mucous membranes.

It is therefore preferred that the composition of the invention should be in a form which ensures contact of the active ingredient with the buccal, sublingual, pharyngeal and/or esophageal mucous membranes.

Preferably, the composition of the invention is in the form of a viscous emulsion, syrup or elixir, a sublingual tablet, a suckable or chewable tablet, softgel or lozenge, chewing gum, a laminated system or patch, hydrogel, adhesive film, hollow fiber, microsphere or other dosage form designed to release the active ingredient in a controlled manner to saliva or to the buccal, pharyngeal and/or esophageal mucous membranes, a fast-dispersing dosage form designed to release the active ingredient rapidly in the oral cavity, or a bioadherent system.

The term "bioadherent system" refers to a solid or liquid dosage form which, at body temperature, exhibits controlled release and bioadherence characteristics. This type of dosage form may be an emulsion which is water in oil in nature and whose internal phase is greater than that of the external phase. Examples of such bioadherent systems may be found in U.S. Pat. No. 5055303.

Active ingredients absorbed by such pre-gastric absorption pass straight into the systemic circulatory system thereby avoiding first pass metabolism in the liver. Accordingly, bioavailability of the active ingredient in this way may also be increased. This means that the dose of active ingredient may be minimized while still producing the desired beneficial effects and unwanted side-effects will therefore also be minimized.

It has been found that fast-dispersing dosage forms can promote pre-gastric absorption of the active ingredient. In addition, clinical studies have shown that such fast dispersing dosage forms, which disintegrate rapidly in the mouth, are easier for patients to take and easier for carers to administer.

One example of a fast-dispersing dosage form is described in U.S. Pat. No. 4855326 in which a melt spinnable carrier agent, such as sugar, is combined with an active ingredient and the resulting mixture spun into a "candy-floss" preparation. The spun "candy-floss" product is then compressed into a rapidly dispersing, highly porous solid dosage form.

U.S. Pat. No. 5120549 discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent, whereby the first solvent is substantially removed resulting in a fast-dispersing matrix.

U.S. Pat. No. 5079018 discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of hydration liquid.

Published International Application No. WO 93/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5298261 discloses fast-dispersing dosage forms which comprise a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) discloses fast-dispersing dosage forms which contain an effervescent disintegration agent designed to effervesce on contact with saliva to provide rapid disintegration of the dosage form and dispersion of the active ingredient in the oral cavity.

The term "fast-dispersing dosage form" therefore encompasses all the types of dosage form described in the preceding paragraphs. However, it is particularly preferred that the fast-dispersing dosage form is of the type described in U.K. Patent No. 1,548,022, that is, a solid fast-dispersing dosage form comprising a network of the active ingredient and a water-soluble or water-dispersible carrier which is inert towards the active ingredient, the network having been obtained by subliming solvent from a composition in the solid state, that composition comprising the active ingredient and a solution of the carrier in a solvent.

It is preferred that the composition of the invention disintegrates within 1 to 60 seconds, more preferably 1 to 30 seconds, particularly 1 to 10 seconds and especially 2 to 8 seconds, of being placed in the oral cavity.

In the case of the preferred type of fast-dispersing dosage form described above, the composition will preferably contain, in addition to the active ingredient, matrix forming agents and secondary components. Matrix forming agents suitable for use in the present invention include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other matrix forming agents suitable for use in the present invention include sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution or suspension. This is especially helpful in the case of active agents that are not sufficiently soluble in water and must, therefore, be suspended rather than dissolved.

Secondary components such as preservatives, antioxidants, surfactants, viscosity enhancers, coloring agents, flavoring agents, pH modifiers, sweeteners or taste-masking agents may also be incorporated into the composition. Suitable coloring agents include red, black and yellow iron oxides and FD & C dyes such as FD & C blue No. 2 and FD & C red No. 40 available from Ellis & Everard. Suitable flavoring agents include mint, raspberry, licorice, orange, lemon, grapefruit, caramel, vanilla, cherry and grape flavors and combinations of these. Suitable pH modifiers include citric acid, tartaric acid, phosphoric acid, hydrochloric acid and maleic acid. Suitable sweeteners include aspartame, acesulfame K and thaumatic. Suitable taste-masking agents include sodium bicarbonate, ion-exchange resins, cyclodextrin inclusion compounds, adsorbates or microencapsulated actives.

Suitable ophthalmologically active compounds that may be utilized in the composition of the invention include anti-glaucoma/intra-ocular pressure lowering compounds such as:

a) alpha-adrenoceptor blocking agents, e.g. apraclonidine, brimonidine, AGN 192836, AGN 193080, etc.

b) beta-adrenoceptor blocking agents, e.g. carteolol, betaxolol, levobunolol, metipranolol, timolol, vaninolol, adaprolol, etc.

c) Miotics, e.g. pilocarpine, carbachol, physostigmine, etc.
d) Sympathomimetics, e.g. adrenaline, dipivefrine, etc.
e) Carbonic anhydrase inhibitors, e.g. acetazolamide, dorzolamide, etc., and
f) Prostaglandins, e.g. PGF-2 alpha or its prodrug latanoprost.

The above compounds may be in the form of free acids or bases or alternatively as salts of these. Combinations of compounds e.g. a beta-adrenoceptor blocking agent with a prostaglandin may be desirable for the optimization of therapy in some instances. The compounds may be formulated as aqueous or non-aqueous (e.g. oil) solutions or suspensions for incorporation into the fast-dispersing dosage form of the invention. Formulations may optionally contain other formulation excipients, for example, mucoadhesives and polymers.

The composition of the invention is particularly suitable for the oral administration of agents for the reduction of intra-ocular pressure. Beta-adrenoceptor blocking agents are the primary therapeutic regimen for the treatment of diseases caused by elevated intra-ocular pressure, such as ocular hypertension and glaucoma, although alpha-adrenoceptor blocking agents have also been used in such treatment. Accordingly, it is preferred that the agent for the reduction of intra-ocular pressure is an alpha-adrenoceptor blocking agent or a beta-adrenoceptor blocking agent and, of these, beta-adrenoceptor blocking agents are particularly preferred.

Beta-adrenoceptor blocking agents lower intra-ocular pressure by reducing the rate of production of aqueous humour, the fluid present in the anterior chamber of the eyeball, and they do this by blocking beta-adrenoceptors in the iris-cilary body.

At present, all beta-adrenoceptor blocking agents used to treat elevated intra-ocular pressure are administered topically to the eye as sterile ophthalmic solutions. Following topical administration, there are four possible mechanisms by which beta blockers could reach their receptor targets: (1) transcorneal diffusion; (2) scleral diffusion; (3) re-absorption from the local vasculature and (4) re-absorption from the systemic circulation. It has traditionally been assumed that transcorneal diffusion is the most important of these mechanisms. However, the work of Sadiq and Vernon (British Journal of Ophthalmology, 1996, 80, 532–535) referred to earlier suggests that, at least for timolol, this assumption may be incorrect as therapeutically active concentrations reached the iris-cilary body following re-absorption from the systemic circulation after sublingual application of an ophthalmic solution of timolol maleate. However, as discussed above, small drops of aqueous formulation are not a convenient way to administer drugs sub-lingually as, not only is it difficult for the patient to deliver the drops to an area which is not clearly visible to the patient, but it is also difficult for the patient to deliver accurate reproducible quantities of the aqueous formulation using a dropper bottle. Accordingly, it is preferred that beta-adrenoceptor blocking agents be incorporated into a single unit dosage form of the type described above which can be easily introduced into the oral cavity and contains an accurately defined dose of the active ingredient.

Suitable beta-adrenoceptor blocking agents include propranolol, acebutolol, alprenolol, atenolol, betaxolol, bufetolol, bufuralol, bunitrolol, bunolol, bupranolol, carteolol, cetamolol, dexpropranolol, labetalol, levobunolol, metipranolol, metoprolol, nadolol, nifenalol, oxprenolol, penbutolol, pindolol, practolol, pronethalol, sotalol, timolol, tolamolol and toliprolol and pharmaceutically acceptable salts thereof. Of these, propranolol, atenolol, betaxolol, bupranolol, carteolol, levobunolol, metipranolol, metoprolol, nadolol, pindolol and timolol and pharmaceutically acceptable salts thereof are preferred and betaxolol, carteolol, levobunolol; metipranolol and timolol and pharmaceutically acceptable salts thereof are particularly preferred. Timolol or a pharmaceutically acceptable salt thereof, especially the maleate, is especially preferred.

The precise quantity of active ingredient will depend on the beta-adrenoceptor blocking agent chosen but will preferably be in the range of 10 to 2000 µg. However, it should be noted that the quantity of the beta-adrenoceptor blocking agent required for ophthalmic treatment is much less than is required for other indications, such as anti-hypertensive applications. For instance, in the case of timolol or a pharmaceutically acceptable salt thereof, this may be present for ophthalmic applications in an amount of 10 to 1000 µg, preferably 50 to 800 µg and especially 100 to 600 µg. The preferred dosage range for timolol maleate is 100 µg to 400 µg, more preferably 150 µg to 380 µg. In the case of timolol in the form of the free base, the preferred dosage range is 100 µg to 300 µg, especially 125 µg to 250 µg. If timolol is used in the form of the free base, it is preferred that this is incorporated into an oil solution before this is, in turn, incorporated into a fast-dispersing dosage form according to the invention. This is in contrast to conventional applications where timolol is used as a non-cardioselective beta blocker at a typical dose of 10 mg.

According to another aspect of the invention there is provided a composition as defined above for use in the treatment of ophthalmic diseases such as diseases caused by elevated intra-ocular pressure and, in particular, ocular hypertension or glaucoma.

According to a further aspect of the invention there is provided a pharmaceutical composition as defined above which comprises bringing a carrier into association with the active ingredient.

The use of a composition for the manufacture of a medicament for the treatment of ophthalmic diseases, such as diseases caused by elevated intra-ocular pressure and, in particular, ocular hypertension or glaucoma, is also provided.

As a further aspect of the invention, there is also provided a method of treating ophthalmic diseases, such as diseases caused by elevated intra-ocular pressure and, in particular, ocular hypertension or glaucoma, which comprises administering a therapeutically effective amount of a composition as defined above to a patient suffering from any of the aforesaid diseases.

DETAILED DESCRIPTION OF THE PREFERRED EMBODIMENTS

The invention is further illustrated by the following example.

EXAMPLE 1

Preparation of a Fast-Dispersing Dosage Form of Timolol (a) Preparation of Timolol 0.1% Dispersion Gelatin (720 g) and mannitol (540 g) were dispersed in a portion of purified water (16.07 kg) by mixing thoroughly in the bowl of a vacuum mixer. The remaining water (1.5 liters) was added under vacuum while mixing using an anchor stirrer. The mix was then heated to 40° C. ±2° C. and homogenized for ten minutes. The mix was cooled down to room temperature. When cooled, a 4500 g portion of the mix was removed into a stainless steel vessel and glycine (360 g), aspartame (90 g), grapefruit flavor (54 g), Opatint yellow (54 g) citric acid (90 g) and timolol maleate (24.7 g) were then added sequentially to this portion while homogenizing using a bench top homogenizer. The remainder of the mix was transferred into a second stainless steel vessel. The mix was homogenized for ten minutes using a bench top mixer to dissolve the drug. Once dispersion of the coloring agent was complete, the homogenized portion of the mix in the first vessel was returned to the mixer bowl together with the mix from the second vessel. The combined mixes were then mixed for at least 20 minutes. The bulk dispersion was then homogenized to ensure that mixing was complete.

(b) Preparation of 250 µg Timolol (as Timolol Maleate) Units 250 mg of the timolol 0.1% dispersion formed in (a) above was dosed into each one of a series of pre-formed blister packs having a pack diameter of 12 mm. The blister laminate comprised 200 µm PVC/30 µm PE/PVDC 90 g per square meter. The product was frozen immediately in a liquid nitrogen freeze tunnel. The frozen product was then stored below –20° C. for a minimum of 24 hours prior to freeze-drying in a freeze drier using a drying temperature of +20° C. and a chamber pressure of 0.5 mbar. The freeze-dried units were then inspected for the presence of critical defects and the remainder of the batch sealed with lidding foil consisting of a paper/foil laminate (20 µm aluminium). Each blister was then coded with a batch number and over-wrapped in a preformed sachet by placing the blister in the sachet and sealing the open end of the sachet completely. Each sachet was then labeled with the product name, batch number, date of manufacture and supplier's name.

Each unit dosage form had the following composition:

| Ingredient | Weight (mg) | % by wt of composition |
|---|---|---|
| Purified Water USP/EP* | 223.16 | 89.264 |
| Timolol maleate | 0.34 | 0.136 |
| Gelatin EP/USNF | 10.00 | 4.000 |
| Mannitol BP/USP | 7.50 | 3.000 |
| Aspartame EP/USN | 1.25 | 0.500 |
| Grapefruit flavor 502.106/A | 0.75 | 0.300 |
| Glycine USP | 5.00 | 2.000 |
| Citric Acid EP/USP | 1.25 | 0.500 |
| Opatint AD-22901 yellow | 0.75 | 0.300 |
| | 250.00 | 100.000 |

*Signifies removed during the lyophilization process.

EXAMPLE 2

Post-dosing Method for Preparation of a Fast-Dispersing Dosage Form of Timolol (a) Preparation of Placebo Units for Post-Dosing Gelatin (40.0 g) and mannitol (30.0 g) were added to a portion of purified water (900.0 g) and dissolved with stirring while heating to 60° C., before cooling to 23° C. A 5% (w/w) sodium hydroxide solution was prepared by weighing the sodium hydroxide (5.0 g) and allowing it to dissolve in 95.0 g of water. This was added dropwise to the bulk mix to adjust the pH to 6.8, and the total amount added was recorded. The remaining quantity of water required was calculated and then added to make up to 100%. 250 mg amounts were dosed into PVC/PVdC blister pockets. The product was then frozen, freeze dried and sealed as described in Example 1.

Each placebo unit dosage form had the following composition:

| Ingredient | Weight (mg) | % by weight composition |
|---|---|---|
| Purified water EP/USP* | q.s. 250 mg | q.s. 100% |
| Gelatin EP/USNF | 10.00 | 4.00 |
| Mannitol EP/USP | 7.50 | 3.00 |
| Sodium Hydroxide EP/USNF | q.s. pH 6.8 | q.s. pH 6.8 |

*signifies removed during the lyophilization process.

(b) Preparation of Timolol Post-Dosing Solution

A 1.196% timolol maleate solution in absolute ethanol was prepared by adding timolol maleate (0.2392 g) to ethanol (18 ml) in a volumetric flask followed by sonication to aid dissolution of the drug. Once completely dissolved, additional ethanol was added to make up to 20.0 ml volume. Using a calibrated syringe, 20 µl of the solution was accurately transferred onto the surface of each dried unit, while in the blister pack. The units were then left for one hour to allow evaporation of the ethanol Each unit ultimately contained 175 µg of timolol.

The final unit dosage form had the following composition:

| Ingredient | Weight |
|---|---|
| Timolol maleate | 0.239 (equivalent to 0.175 mg timolol base) |
| Gelatin EP/USNF | 10.00 |
| Mannitol EP/USP | 7.50 |
| Sodium Hydroxide EP/USNF | q.s. pH 6.8 (approximately 0.01 mg) |

EXAMPLE 3

Comparative Safety and Efficacy Study

The primary aim of this study was to assess the efficacy and side effect profile of the timolol maleate formulation of Example 2 in comparison with the commercially available eye drop formulation of timolol maleate sold under the trade mark "Timoptol" by Merck Sharp and Dohme Ltd. of Hertford Road, Hoddesdon, Hertfordshire EN11 9BU in reducing the intra-ocular pressure of patients presenting with raised intra-ocular pressure.

An open label, single-dose, randomized, 2-way crossover, patient study was performed as follows.

Three patients of either sex, aged between 18 and 70 years, with raised intra-ocular pressure (>21 mm Hg and ≦30 mm Hg) each received two treatments as follows:

175pg formulation of Example 2 0.5% "Timoptol" formulation eye drops to one eye selected at random and without occlusion.

(estimated to be equivalent to a dose of 175 µg timolol)

The patients were given a single dose of each preparation separated by a period of at least 7 days between the treatments. On each dosing day, the intra-ocular pressure was measured pre-dose, and at 2 hours and 24 hours post dose. The person measuring intra-ocular pressure was unaware which of the two treatments had been administerd. Pulse rate and blood pressure was measured pre-dose and at 20, 40, 60 and 125 minutes post dose.

The results of the intra-ocular pressure (IOP) measurements are given in Tables 1 and 2 below.

TABLE 1

Example 2 (175 μg) Treatment

| Patient # | IOP before (mmHg) | | IOP after (mmHg) | | IOP decrease (mmHg) | |
|---|---|---|---|---|---|---|
| | Right eye | Left eye | Right eye | Left eye | Right eye | Left eye |
| 001 | 25.0 | 25.3 | 19.6 | 20.0 | 5.4 | 5.3 |
| 002 | 25.6 | 27.0 | 18.0 | 19.0 | 7.6 | 8.0 |
| 003 | 23.6 | 22.6 | 18.3 | 17.3 | 5.3 | 5.3 |
| Mean | 24.7 | 25.0 | 18.6 | 18.8 | 6.1 | 6.2 |

TABLE 2

Timoptol (0.50%) Eyedrops Treatment

| # | IOP before (mmHg) | | IOP after (mmHg) | | IOP decrease (mmHg) | |
|---|---|---|---|---|---|---|
| | Treated eye | Untreated | Treated eye | Untreated | Treated eye | Untreated |
| 001 | 23.3 | 25.0 | 17.3 | 18.6 | 6.0 | 6 |
| 002 | 24.0 | 22.6 | 11.0 | 18.6 | 13.0 | 4 |
| 003 | 19.3 | 19.0 | 13.0 | 13.6 | 6.3 | 5 |
| Mean | 22.2 | 22.2 | 13.8 | 16.9 | 8.4 | 5 |

It is apparent from Tables 1 and 2 that, when patients were treated with the formulation of Example 2, a significant reduction in intra-ocular pressure was observed in both eyes. This result is consistent with systemic absorption of the active ingredient.

When the patients were treated with the "Timoptol" eye drop formulation in one eye, patient #002 experienced a much greater reduction in intra-ocular pressure in the treated eye than in the untreated eye. However, such a significant difference was not observed in patients #001 and #003. This suggests that some systemic absorption also occurs when the "Timoptol" eye drop formulation is used, probably as a result of the treated eye not being occluded and the drops therefore draining from the surface of the eye, down the nasal lachrymal duct, from which the active ingredient will be absorbed and transferred to the other eye via the systemic circulatory system. However, the quantity of active ingredient which may be absorbed via this route clearly cannot be accurately controlled.

The blood pressure measurements showed no clinically significant, or clinically concerning, drop in blood pressure associated with the hypotensive effects of systemic timolol.

The normal intra-ocular pressure range is 10–20 mm Hg whereas individuals with intra-ocular pressure between 21–30 mm Hg will generally develop optic disc changes at a rate of 0.5–1% per year over 5–15 years. Moreover, visual field damage occurs in 28% of patients with intra-ocular pressure in excess of 30 mm Hg. Thus, in a patient with optic disc changes or visual field defects, it is normal practice to reduce intra-ocular pressure to prevent blindness. To be effective, treatment should bring the intra-ocular pressure down to the normal range of 10–20 mm Hg. Thus, it is clear from Table 1 that treatment with the formulation of Example 2 is clinically effective. Moreover, since the blood pressure measurements were satisfactory, it would appear that treatment with the formulation of Example 2 does not cause serious hypotensive side effects.

I claim:

1. A method of treating ophthalmic diseases comprising the steps of:

a) preparing a fast dispersing dosage form which disintegrates within 1 to 60 seconds of being placed in the oral cavity by subliming solvent from a solid composition comprising an ophthalmologically active compound, a solvent and a water soluble or water dispersable carrier which is inert towards the active compound; and b) orally administering said fast dispersing dosage form composition to a patient.

2. The method according to claim 1 wherein the step of preparing comprises the step of formulating the composition to promote absorption of the ophthalmologically active compound through the buccal, sublingual, pharyngeal and/or esophageal mucous membranes.

3. The method according to claim 1 in which the ophthalmologically active compound is an agent for the reduction of intra-ocular pressure.

4. The method according to claim 3 in which the agent for the reduction of intra-ocular pressure is a beta-adrenoceptor blocking agent.

5. The method according to claim 4 in which the beta-adrenoceptor blocking agent is selected from propranolol, acebutolol, alprenolol, atenolol, betaxolol, bufetolol, bufuralol, bunitrolol, bunolol, bupranolol, carteolol, cetamolol, dexpropranolol, labetalol, levobunolol, metipranolol, metoprolol, nadolol, nifenalol, oxprenolol, penbutolol, pindolol, practolol, pronethalol, sotalol, timolol, tolamolol and toliprolol and pharmaceutically acceptable salts thereof.

6. The method according to claim 5 in which the beta-adrenoceptor blocking agent is selected from propranolol, atenolol, betaxolol, bupranolol, carteolol, levobunolol, metipranolol, metoprolol, nadolol, pindolol and timolol and pharmaceutically acceptable salts thereof.

7. The method according to claim 6 in which the beta-adrenoceptor blocking agent is timolol or a pharmaceutically acceptable salt thereof.

8. The method according to claim 1 in which timolol or a pharmaceutically acceptable salt thereof is present in said fast dispersing dosage form in an amount of 10 to 1000 μg.

9. The method as defined in claim 1 wherein the fast dispersing dosage form is a medicament for the treatment of ocular hypertension.

10. The method as defined in claim 1 wherein the fast dispersing dosage form is a medicament for the treatment of glaucoma.

* * * * *